United States Patent [19]

Jurisson et al.

[11] Patent Number: 5,118,797
[45] Date of Patent: Jun. 2, 1992

[54] RHENIUM TRIS DIOXIME COMPLEXES

[75] Inventors: Silvia Jurisson, Dunellen; Karen E. Linder, Highland Park; Lynn C. Francesconi, Cinnaminson, all of N.J.

[73] Assignee: E. R. Squibb & Sons, Inc., Princeton, N.J.

[21] Appl. No.: 398,879

[22] Filed: Aug. 28, 1989

[51] Int. Cl.$^5$ .................. C07F 13/00; A61K 43/00
[52] U.S. Cl. .................. 534/10; 556/37; 556/45; 424/1.1
[58] Field of Search .................. 424/1.1; 534/10, 14, 534/15; 556/37, 45

[56] References Cited

U.S. PATENT DOCUMENTS

| | | | |
|---|---|---|---|
| 4,387,087 | 6/1983 | Deutsch et al. | 424/1.1 |
| 4,419,339 | 12/1983 | Neirinckx | 424/1.1 |
| 4,615,876 | 10/1986 | Troutner et al. | 424/1.1 |
| 4,705,849 | 11/1987 | Nunn et al. | 534/14 |
| 4,714,605 | 12/1987 | Feld et al. | 534/14 X |
| 4,789,543 | 12/1988 | Linder | 424/1.1 |
| 4,795,626 | 1/1989 | Deutsch et al. | 424/1.1 |

FOREIGN PATENT DOCUMENTS 311891 4/1989 European Pat. Off. .

OTHER PUBLICATIONS

Fergusson, J. E. et al., "α-Furildioxime Complexes of Rhenium", *Inorg. Chemistry* (1963) p. 290.
Bailey, R. A. et al., "Compounds Formed on the Reduction of ReO$_4$. . . ", *J. Inorg. Nucl. Chem.* (1969) vol. 31, pp. 2031-2037.
Maun et al., "Investigations in the Chemistry of Rhenium", *J. Am. Chem. Soc.* (1950) vol. 72, p. 2254.
Jasim et al., "New Reagents for the Detection of Technetium", *Talanta* (1959) vol. 2, pp. 93-95.
Meloche et al., "Spectrophotometric Determination of Rhenium", *Anal. Chem.*, vol. 29, No. 4, pp. 527-529 (1957).
Colton, R. et al., *UK Atomic Energy Authority, Research Group Report,* #AERE-R3746, "The Spectrophotometric Determination of Technetium with Furil-α-Dioxime" (Chem. Div., AERE, Harwell Brekshire) Jun. 1961.
Boston et al., *J.A.C.S.*, vol. 95, pp. 4163-4168 (1973), "Encapsulation Reactions. Synthesis and Study of Clathro Chelates Derived from Dimethylglyoxime, Cobalt and Lewis Acids".
Gillard et al., *J. of Chem. Soc.*, (1963), pp. 6041-6044, "Hydrogen Bonding in Complexes of Dimethylglyoxime with Cobalt (III)".
*Inorganic Synthesis,* vol. 17, Chap. 3, pp. 139-147 (1978) "Other Transition Metal Compounds", Jackel et al.
CA 86(12): 83217a, "Improvement of Some Procedures for Photometric Determination of Rhenium", Stefanov et al., (1976).
CA 95(12):107698, "Infrared Spectroscopic Study . . . Rhenium with Analytical Organic Reagents", Plastinina et al., (1981).

*Primary Examiner*—Robert L. Stoll
*Assistant Examiner*—John M. Covert
*Attorney, Agent, or Firm*—Theodore R. Furman, Jr.

[57] ABSTRACT

Rhenium tris dioxime complexes are useful in the synthesis of boronic acid adducts of rhenium dioxime complexes which are useful as radiotherapeutic agents.

9 Claims, No Drawings

RHENIUM TRIS DIOXIME COMPLEXES

FIELD OF THE INVENTION

This invention relates to rhenium tris dioxime complexes and their use as intermediates in the preparation of boronic acid adducts of rhenium dioxime complexes. The boronic acid adducts of rhenium dioxime complexes are useful in radiotherapy.

BACKGROUND OF THE INVENTION

Boronic acid adducts of rhenium dioxime complexes useful in radiotherapy have been described in European Patent Application 311,891 published Apr. 19, 1989 and have the formula $ReX(Y)_3Z$ wherein X is an anion, Y is a vicinal dioxime having the formula $$HO-N=\underset{R_1}{\underset{|}{C}}-\underset{R_2}{\underset{|}{C}}=N-OH$$

or a pharmaceutically acceptable salt thereof, and $R_1$ and $R_2$ are each independently hydrogen, halogen, alkyl, aryl, amino or a 5 or 6-membered nitrogen or oxygen containing heterocycle, or together $R_1$ and $R_2$ are $-(CR_8R_9)_n-$ wherein n is 3, 4, 5 or 6 and $R_8$ and $R_9$ are each independently hydrogen or alkyl;

Z is a boron derivative having the formula $B-R_3$ wherein $R_3$ is hydroxy, alkyl, alkenyl, cycloalkyl, cycloalkenyl, alkoxy, carboxyalkyl (preferably having 2 to 10 carbons), carboxyalkenyl (preferably having 4 to 19 carbons), hydroxyalkyl, hydroxyalkenyl, alkoxyalkyl, alkoxyalkenyl, haloalkyl, haloalkenyl, aryl, arylalkyl or $(R_4R_5N)$alkyl and $R_4$ and $R_5$ are each independently hydrogen, alkyl, or arylalkyl, or $R_4$ and $R_5$ when taken together with the nitrogen atom to which they are attached form a 5 or 6-membered nitrogen containing heterocycle. The boron derivative "Z" can be thought of as a "cap" for the dioximes at one end of the molecule, through boron-oxygen covalent bonds. The above European Patent Application describes the formation of the "boron capped" rhenium dioxime complexes utilizing rhenium in the plus 3, plus 4, plus 5 or plus 7 oxidation state. European Patent Application 311,891 describes compounds in which rhenium is available in the plus 3 oxidation state such as $ReCl_3(CH_3CN)(PPh_3)_2$ and $[Re_2Cl_8](NBu_4)_2$ wherein Ph=phenyl and Bu=butyl; Re(IV) as $K_2ReCl_6$ and Re(VII) as $NH_4ReO_4$ or $KReO_4$; Re(V) as $[ReOCl_4](NBu_4)$, $[ReOCl_4](AsPh_4)$, $ReOCl_3(PPh_3)_2$ and as $ReO_2$-(pyridine)$_4^\oplus$.

The complexes of European Patent Application 311,891 are prepared with Re(III), Re(IV), Re(V) or Re(VII) ions (in the form of a salt) combined with a source of anion, a boronic acid derivative having the formula $$R_7O-\underset{R_3}{\underset{|}{B}}-OR_7$$

or a pharmaceutically acceptable salt thereof, wherein $R_7$ is hydrogen, alkyl or aryl, and a dioxime having the formula $$HO-N=\underset{R_1}{\underset{|}{C}}-\underset{R_2}{\underset{|}{C}}=N-OH.$$

or a pharmaceutically acceptable salt thereof.

More specifically, the boronic acid adducts of rhenium dioxime complexes of European Patent Application 311,891 were prepared from either Re(III), as $ReCl_3(CH_3CN)(PPh_3)_2$, Re(IV), as $ReCl_6^2$, or Re(VII), as $ReO_4^-$. When the complexes were prepared from Re(III), a reaction time of 15-22 hours was required to form the compounds. When the complexes were prepared from Re(VII), strongly acidic conditions were required, and yields were 0.7 to 5%.

When working with radioactive isotopes of rhenium that have short half-lives, it is important that short reaction times and good yields be obtained. The procedures described in European Patent Application 311,891 either take a long time, give poor yields, or are carried out under strongly acidic conditions. It would be advantageous to devise a high yield procedure for the preparation of these boron capped rhenium dioxime compounds that does not take a long time to carry out. If the compounds could be made in quantitative yield, a separation step could also be avoided. If the reaction conditions were gentle, capping boron ligands that are heat or acid sensitive could be used.

It has now been found that the "boron capped" rhenium dioxime complexes can be formed under very mild conditions if the complexes of the present invention are used as starting materials. The formation of the boron capped rhenium complexes from the complexes of the present invention requires less than one hour, is carried out under mild reaction conditions, and is virtually quantitative. The compounds of this invention can also be capped by other Lewis acids such as derivatives of silicon, aluminum, titanium and tin.

BRIEF DESCRIPTION OF THE INVENTION

Rhenium dioxime complexes incorporating radioactive isotopes of rhenium and having the formula $ReX(Y)_3$      I are useful as intermediates for preparing "capped" rhenium dioxime compounds which are useful as agents for radiotherapy. In formula I and throughout the specification, the symbols are defined as below X is an anion, Y is a vicinal dioxime having the formula $$OH-N=\underset{R_1}{\underset{|}{C}}-\underset{R_2}{\underset{|}{C}}=N-OH \qquad II$$

or a pharmaceutically acceptable salt thereof wherein $R_1$ and $R_2$ are each independently hydrogen, halogen, alkyl, aryl, amino or taken together a 5 or 6-membered nitrogen, oxygen or sulfur containing heterocycle, or together $R_1$ and $R_2$ are $-(CR_8R_9)n-$ wherein n is 3, 4, 5 or 6 and $R_8$ and $R_9$ are each independently hydrogen or alkyl;

The terms "alkyl" and "alkoxy" refer to both straight and branched chain saturated hydrocarbon groups.

Those groups having 1 to 10 carbon atoms are preferred.

The term "alkenyl" refers to both straight and branched chain hydrocarbon groups containing one or more points of unsaturation. Those groups having 2 to 10 carbon atoms are preferred.

The term "aryl" refers to phenyl and substituted phenyl. Preferred are phenyl and phenyl substituted with 1, 2 or 3 alkyl, haloalkyl, aminoalkyl, alkylaminoalkyl, dialkylaminoalkyl, alkoxy, alkoxyalkyl, halogen, amino, hydroxy, or formyl groups.

The terms "halide", "halo" and "halogen" refer to atoms or anions of fluorine, chlorine, bromine and iodine.

The expression "5 or 6-membered nitrogen containing heterocycle" refers to all 5 and 6-membered rings containing at least one nitrogen or oxygen atom. Exemplary groups have the formula

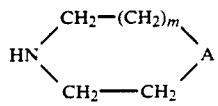

wherein m is 0 or 1 and A is oxygen, sulfur, N—$R_6$ or CH—$R_6$ wherein $R_6$ is hydrogen, alkyl, aryl or arylalkyl. Such groups include pyrrolidinyl, piperidinyl, morpholinyl, piperazinyl, 4-alkylpiperazinyl, 4-alkylpiperidinyl, 3-alkylpyrrolidinyl, 1,4-dioxanyl and furanyl. Also included within the expression "5 or 6-membered nitrogen containing heterocycle" are aromatic groups. Exemplary aromatic groups are pyrrolyl, imidazolyl, oxazolyl, pyrazolyl, pyridinyl, pyrimidinyl, and furanyl groups. The above groups can be linked via a hetero atom or a carbon atom.

The expression "5 or 6-membered nitrogen, oxygen or sulfur containing heterocycle" refers to all 5 and 6-membered rings containing at least one nitrogen, sulfur or oxygen atom. Exemplary groups are those described above under the definition of the expression "5 or 6-membered nitrogen containing heterocycle". Additional exemplary groups are 1,4-dioxanyl and furanyl.

DETAILED DESCRIPTION OF THE INVENTION

All of the examples and the following process description involve the use of "carrier rhenium". The phrase "carrier rhenium" means that the rhenium compounds used contain non-radioactive rhenium at concentrations of about $10^{-7}$ to $10^{-3}$ M. This invention could be extended to include "no carrier added" rhenium, as rhenium-186 or rhenium-188 from the W/Re generator system being developed and described in PCT Application 88/03697 published on May 19, 1988.

Preparation of the complexes of this invention can best be accomplished using rhenium in the 3, 4, 5 or 7 oxidation states. Examples of compounds in which rhenium is in the +3 oxidation state are $ReCl_3(CH_3CN)(PPh_3)_2$ and $(Bu_4N)_2[ReCl_8]$ wherein Ph=phenyl and Bu=butyl. Re(IV) is available as $K_2[ReCl_6]$ or any other salt of $ReCl_6^{2-}$, Re(V) as $(Bu_4N)ReOCl_4$, $(Ph_4As)ReOCl_4$, $ReOCl_3(PPh_3)_2$ and $ReO_2(pyridine)_4+$, and Re(VII) as $NH_4ReO_4$ or $KReO_4$. Other Re(III), Re(IV), Re(V) and Re(VII) reagents known to those skilled in the art can also be used.

To prepare complexes of this invention, the Re(III), Re(IV), Re(V) or Re(VII) reagent is combined with a source of anion, and a dioxime having the formula

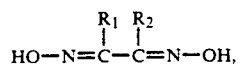

or a pharmaceutically acceptable salt thereof.

The source of the anion moiety (X) can be water or it can be an acid or salt which dissociates to release an appropriate anion. Exemplary anionic moieties are hydroxyl, halide, isothiocyanato (N=C—S$^-$) and thiocyanato (S=C=N$^-$). The preferred anionic moieties are the halides, and chloride is the most preferred halide. If the source of the anion is not water, the source should be present in an appropriate concentration to compete effectively with any water that may be present during the reaction. It has been found that the source of anion should be present in the reaction mixture in a concentration of about 0.1 to 1.0 molar.

The formation of the complex generally requires that the mixture of Re(III), Re(IV), Re(V) or Re(VII) reagent, source of anion, and dioxime is reacted/heated at about 25° C. to 100° C. for about 5 minutes to about 8 hours.

If Re(IV), Re(V) or Re(VII) containing starting materials are employed, then the reaction mixture may also contain a reducing agent. Stannous ion (in the form of a stannous salt such as a stannous halide) is the preferred reducing agent. The reducing agent should be present in a concentration in excess of that needed to reduce the starting material to Re(III).

When $^{186}Re$ or $^{188}Re$ kits are prepared using radioactive $^{186}Re$ or $^{188}Re$, various additives can be included as part of the complexing reaction to enhance the radiochemical purity (the percentage of the total radioactivity present in the desired form). These additives might be chelating agents, catalysts, and solubilization aids (such as cyclodextrins, surfactants, buffers, etc.). The additive should, of course, be pharmaceutically acceptable. Exemplary additives include diethylenetriaminepentaacetic acid (DTPA), ethylene glycol-bis($\alpha$-aminoethyl ether)-N,N'tetraacetic acid (EGTA), ethylenediamine tetraacetic acid (EDTA), citric acid, tartaric acid, malonic acid, etc. Other additives may also be used.

It is convenient to prepare the complexes of this invention at or near, the site where they are to be used. To facilitate this requirement, a kit having all of the components, (other than the Rhenium ion), needed to prepare the Rhenium dioxime complexes of formula I is an integral part of this invention. Such a kit contains a source of anion, a dioxime of formula II, or a pharmaceutically acceptable salt thereof, and a reducing agent. It may optionally contain a complexing agent and/or catalyst.

Preparation of the Rhenium dioxime complex from such a kit involves the addition of the source of rhenium, in aqueous solution, followed by a heating step. Generally, heating at about 50° to 100° C. for about 30 minutes to about 3 hours is required. To optimize the stability of the kit, and to optimize the radiochemical purity of the labeled product, the pH of the kit should be adjusted to fall within the range of about 2.0 to 5.5 using a pharmaceutically acceptable acid or base (e.g., hydrochloric acid or sodium hydroxide). Preferably, the pH of the kit will be about 3.0. It is also preferred that the kit be in lyophilized form.

To isolate the desired complex, separation methods well known in the art may be required. As an example, the ReX(Y)$_3$ can be separated from the other kit ingredients by sorbing the kit constituents onto a plug of PRP-1 reverse-phase resin, washing with saline and 25% ethanol/saline, and eluting the product with ethanol. The ReX(Y)$_3$ can be capped with boronic acids under the mild conditions, described herein, to prepare the ReX(Y)$_3$Z compounds.

The following examples are specific embodiments of this invention.

EXAMPLE 1

Re(chloride) (cyclohexanedionedioxime)$_3$

ReCl$_3$(CH$_3$CN) (PPh$_3$)$_2$ (0.15 g, 0.17 mmol), cyclohexanedionedioxime (0.10 g, 0.70 mmol) and a stir bar were placed in a 50 ml, 3-necked round bottom flask equipped with a condenser and a gas inlet tube. The apparatus was flushed with N$_2$, and CH$_2$Cl$_2$ (30 ml) was added. The mixture was refluxed under N$_2$ for 3–4 hours. The solution turned orange-brown in color. The reaction mixture was then filtered, concentrated by evaporation (to ca. 2–3 ml), and purified by silica gel chromatography. Elution with CH$_2$Cl$_2$ displaced first unreacted starting compound and then the orange band of ReCl(CDO)$_3$. Addition of an equal volume of hexane yielded ReCl(CDO)$_3$ on evaporation. Yield: 0.095 g (45%). Elemental analyses. Calculated for ReClC$_{18}$H$_{28}$N$_6$O$_6$: C, 33.46; H, 4.34; N, 13.01. Found: C, 33.41; H, 4.18; N, 12.79. Mass spectral analyses: MW = 646. Found (M+H)$^+$ = 647 and (M−H)$^-$ = 645.

EXAMPLE 2

Re(chloride) cyclohexanedionedioxime)$_3$(phenylboron)

ReCl(CDO)$_3$ (0.00361 g, 0.0056 mmol) was dissolved in CH$_3$CN (4 ml). HCl (0.5 $\underline{M}$, 1 ml) and phenylboric acid (0.00201 g, 0.0165 mmol) were added, and the resultant mixture was heated to ca. 50° C. for 30 minutes. HPLC (PRP-1, 90/10 CH$_3$CN/0.1 $\underline{M}$ NH$_4$OAc (pH 4.6), 2 ml/min, and 450 nm) was used to monitor the progress of the reaction. Under these conditions, ReCl(CDO)$_3$ has a retention time of 4.14 minutes and the product, ReCl(CDO)$_3$BPh, has a retention time of 5.35 minutes. The reaction was virtually complete within 20 minutes. 10 ml of H$_2$O were added to the reaction mixture. The ReCl(DCO)$_3$BPh was extracted with 10 ml of CH$_2$Cl$_2$. The CH$_2$Cl$_2$ was dried through anhydrous Na$_2$SO$_4$ and the solution allowed to crystallize. 0.00402 g (98% yield) of product was isolated.

EXAMPLE 3

Re(chloride) cyclohexanedionedioxime)$_3$(butylboron)

ReCl(CDO)$_3$BBu was prepared using the method described in Example 2, substituting butylboronic acid [(OH)$_2$BBu] for phenylboric acid. HPLC (Licrosorb RP-18, 90/10 CH$_3$CN/0.1 $\underline{M}$ NH$_4$OAc (pH 4.6), 1 ml/min and 450 nm) was used to monitor the progress of the reaction. Under these conditions, ReCl(CDO)$_3$ has a retention time of 3.7 minutes and the product, ReCl(CDO)$_3$BBu, has a retention time of 6.5 minutes. The reaction was complete within 20 minutes with the yield being close to quantitive (as determined by silica gel TLC/CH$_2$Cl$_2$ and HPLC).

EXAMPLE 4

Re(chloride) cyclohexanedionedioxime)$_3$methylboron)

ReCl(CDO)$_3$BMe was prepared using the method described in Example 2, substituting methylboronic acid (OH)$_2$BMe for butylboronic acid. HPLC (Licrosorb RP-18, 90/10 CH$_3$CN/0.1 $\underline{M}$ NH$_4$OAc (pH 4.6), 1 ml/min and 450 nm) was used to monitor the progress of the reaction. Under these conditions, ReCl(CDO)$_3$BMe has a retention time of 4.25 minutes, compared to 3.7 minutes for ReCl(CDO)$_3$. The reaction was complete within 20 minutes with the yield being close to quantitative (by silica gel TLC/CH$_2$Cl$_2$ and HPLC).

What is claimed is:

1. Dioxime complexes of rhenium and isotopes of rhenium having the formula

ReX(Y)$_3$ wherein
X is a halide and
Y is a vicinal dioxime having the formula $$\begin{array}{cc} R_1 & R_2 \\ | & | \\ HO-N=C-C=N-OH \end{array}$$

wherein R$_1$ and R$_2$ are each independently hydrogen, halogen, alkyl, aryl, amino or a 5 or 6 membered nitrogen, oxygen or sulfur containing heterocycle, or together R$_1$ and R$_2$ are —(CR$_8$R$_9$)$_n$— wherein n is 3, 4, 5 or 6 and R$_8$ and R$_9$ are each independently hydrogen or alkyl.

2. A dioxime complex in accordance with claim 1 wherein X is chloride or bromide.

3. A dioxime complex in accordance with claim 1 wherein X is chloride.

4. A dioxime complex in accordance with claim 1 wherein Y is dimethylglyoxime, 1,2-cyclohexanedionedioxime, 1,2-ethanedionedioxime, α-furyldioxime, 1,2-cyclopentanedionedioxime or 3-methyl-1,2-cyclohexanedionedioxime.

5. A dioxime complex in accordance with claim 1 wherein Y is dimethylglyoxime.

6. A dioxime complex in accordance with claim 1 wherein Y is 1,2-cyclohexanedionedioxime.

7. A dioxime complex in accordance with claim 1 wherein Y is 1,2-ethanedionedioxime.

8. A complex in accordance with claim 1 having the name Re(chloride) (cyclohexanedionedioxime)$_3$.

9. A complex in accordance with claim 1 having the name Re(chloride) (dimethylglyoxime)$_3$.

* * * * *